US012729230B2

(12) United States Patent
Ji et al.

(10) Patent No.: US 12,729,230 B2
(45) Date of Patent: Sep. 8, 2026

(54) DEVELOPMENT AND USE OF INTERLEUKIN 15 MUTANT POLYPEPTIDE

(71) Applicant: Suzhou Forlong Biotechnology Co., Ltd., Jiangsu (CN)

(72) Inventors: En Ji, Jiangsu (CN); Chunyu Wang, Jiangsu (CN)

(73) Assignee: Suzhou Forlong Biotechnology Co., Ltd., Jiangsu (CN)

( * ) Notice: Subject to any disclaimer, the term of this patent is extended or adjusted under 35 U.S.C. 154(b) by 458 days.

(21) Appl. No.: 18/564,329

(22) PCT Filed: May 23, 2022

(86) PCT No.: PCT/CN2022/094443
§ 371 (c)(1),
(2) Date: Nov. 27, 2023

(87) PCT Pub. No.: WO2022/247778
PCT Pub. Date: Dec. 1, 2022

(65) Prior Publication Data

US 2026/0055153 A1 Feb. 26, 2026

(30) Foreign Application Priority Data

May 28, 2021 (CN) .......................... 202110591118.6

(51) Int. Cl.
*C07K 14/54* (2006.01)
*A61K 38/00* (2006.01)

(52) U.S. Cl.
CPC .......... *C07K 14/5443* (2013.01); *A61K 38/00* (2013.01)

(58) Field of Classification Search
CPC ............................ C07K 14/5443; C12N 15/00
See application file for complete search history.

(56) References Cited

U.S. PATENT DOCUMENTS

| | | | |
|---|---|---|---|
| 9,676,857 | B2 | 6/2017 | Dimitrov |
| 10,000,576 | B1 | 6/2018 | Weisser |
| 2006/0074225 | A1 | 4/2006 | Chamberlain |
| 2012/0244578 | A1 | 9/2012 | Kannan |
| 2013/0177555 | A1 | 7/2013 | Wilkinson |
| 2015/0050278 | A1 | 2/2015 | Dimitrov |
| 2015/0353636 | A1 | 12/2015 | Parren |
| 2018/0118828 | A1 | 5/2018 | Bernett |
| 2019/0092830 | A1 | 3/2019 | Wang |
| 2019/0359684 | A1 | 11/2019 | Bernett |
| 2020/0040083 | A1 | 2/2020 | Bernett |
| 2021/0206847 | A1 | 7/2021 | Ying |

FOREIGN PATENT DOCUMENTS

| | | |
|---|---|---|
| CA | 3098930 | 3/2020 |
| CN | 105229026 A | 1/2016 |
| CN | 106380521 A | 2/2017 |
| CN | 106659775 | 5/2017 |
| CN | 107880136 A | 4/2018 |
| CN | 108101988 | 6/2018 |
| CN | 109468278 | 3/2019 |
| CN | 109503718 | 3/2019 |
| CN | 109705211 | 5/2019 |
| CN | 110551223 | 12/2019 |
| CN | 111132733 A | 5/2020 |
| CN | 111303296 | 6/2020 |
| CN | 111699200 | 9/2020 |
| CN | 111741977 | 10/2020 |
| CN | 112105645 A | 12/2020 |
| CN | 112584851 | 3/2021 |
| CN | 113185600 | 7/2021 |
| EP | 3677595 | 7/2020 |
| JP | 2013511281 | 4/2013 |
| JP | 2013537416 | 10/2013 |
| JP | 2013541335 | 11/2013 |
| JP | 2020529832 | 10/2020 |
| JP | 2020536586 | 12/2020 |
| WO | 2005085282 | 9/2005 |
| WO | 2005086798 | 9/2005 |
| WO | 2010085495 | 7/2010 |
| WO | 2012107417 | 8/2012 |
| WO | 2013138643 | 9/2013 |
| WO | 2016004060 | 1/2016 |
| WO | 2016008973 A1 | 1/2016 |
| WO | 2016095642 A1 | 6/2016 |
| WO | 2018039626 | 3/2018 |
| WO | 2019126464 | 6/2019 |
| WO | 2019204665 | 10/2019 |
| WO | 2019213517 | 11/2019 |
| WO | 2019246379 | 12/2019 |
| WO | 2020232427 | 11/2020 |
| WO | 2020252264 | 12/2020 |
| WO | 2021030688 | 2/2021 |
| WO | 2021119429 | 6/2021 |

(Continued)

OTHER PUBLICATIONS

Avi Ashkenazi et al. "Immunoadhesins as research tools and therapeutic agents," Current Opinion in Immunology, vol. 9, issue 2 (Apr. 1997) pp. 195-200.
Borrok, M.J et al., "Chain A, Ig Gamma-1 Chain C Region, PDB: 3S7G_A, 227aa Linear", genBank, (Oct. 10, 2012), URL: NCBI, 1 page.
Burvenich Ingrid J G, et al., "Cross-species analysis of Fc engineered anti-Lewis-Y human IgG1 variants in human neonatal receptor transgenic mice reveal importance of S254 and Y436 in binding human neonatal Fc receptor", «MAbs» 2016, 12 pages.
Chunyu Wang et al. "Engineered Soluble Monomeric IgG1 Fc with Significantly Decreased Non-Specific Binding," Frontiers in Immunology, vol. 8, article 1545 (Nov. 2017) pp. 1-8.
Ferrara et al., PNAS (2011), vol. 108, No. 31, pp. 12669-12674. (Year: 2011).

(Continued)

*Primary Examiner* — Prema M Mertz
(74) *Attorney, Agent, or Firm* — Ice Miller LLP

(57) ABSTRACT

Provided in the present application are an IL-15 mutant polypeptide, and a preparation method therefor and the use thereof. Further provided are a nucleic acid encoding the IL-15 mutant polypeptide, a vector containing the nucleic acid, and a host cell.

19 Claims, 3 Drawing Sheets

Specification includes a Sequence Listing.

(56) References Cited

FOREIGN PATENT DOCUMENTS

| WO | 2021119516 | 6/2021 |
|---|---|---|
| WO | 2022247778 | 12/2022 |

OTHER PUBLICATIONS

Ferrara, C. et al., "Chain A, Human Fc Fragment, PDB: 3SGJ A, 225aa Linear", genBank, (Oct. 10, 2012), URL: NCBI, 1 page.
Frederick M. Ausubel et al. "Short Protocols in Molecular Biology. A Compendium of Methods from Current Protocols in Molecular Biology," Current Protocols in Molecular Biology (Jun. 1991). 2 pages.
Giri, J. G. et al. "Utilization of the beta and gamma chains of the IL-2 receptor by the novel cytokine IL-15," The Embo Journal, vol. 13, issue 12 (Jun. 1, 1994) pp. 2822-2830.
Grabstein, Kenneth H. et al. "Cloning of a T Cell Growth Factor that Interacts with the β Chain of the Interleukin-2 Receptor," Science, vol. 264, issue 5161 (1994) pp. 965-968.
Han Kai-ping, et al., "IL-15:IL-15 receptor alpha superagonist complex: High-level co-expression in recombinant mammalian cells, purification and characterization," Cytokine, vol. 56, No. 3, pp. 804-809, Oct. 22, 2011.
Holliger, Philipp, et al. "Engineered Antibody Fragments and the Rise of Single Domains," Nature Biotechnology, vol. 23, issue 9 (Oct. 2005) pp. 1126-1136.
International Preliminary Report on Patentability (Form PCT/IB/373) for International Patent Application No. PCT/CN2022/094443, issued from the International Searching Authority, date of mailing Nov. 21, 2023, 6 pages.
International Search Report (Form PCT/ISA/210) for International Patent Application No. PCT/CN2022/094443, issued from the International Searching Authority, date of mailing Aug. 26, 2022, 13 pages.
Jinghe Huang et al. "Broad and potent HIV-1 neutralization by a human antibody that binds the gp41-gp120 interfac," Nature, vol. 515, issue 7525 (Nov. 6, 2014) pp. 138-142.
Lu, J., et al.: "Chain A. Ig Comma-1 Chain C Region", PDB: 4X4M_A, 219aa Linear (NCBI Genbank), Apr. 8, 2015 1-2.
Matsumiya, S. et al.: "Chain A, Ig Gamma-1 Chain C. Region" PDB: 2DTS_A, 223aa Linear (NCBI Genbank), Oct. 10, 2012, 1-2.
R.J. Massey "Catalytic antibodies catching on," Nature, vol. 328 (1987) pp. 457-458.
Saerens, Dirk et al. "Single-domain antibodies as building blocks for novel therapeutics," Current Opinion in Pharmacology, vol. 8, issue 5 (Oct. 2008) pp. 600-608.
Silva-Martin, N. et al."Chain A, Ig Gamma-1 Chain C Region" PDB: 4CDH_A, 255aa Linear (NCBI Genbank), Feb. 25, 2015, 1-2.
Steven M. Chamow et al. "Immunoadhesins: principles and applications," Trends in Biotechnology, vol. 14, issue 2 (Feb. 1996) pp. 52-60.
Tianlei Ying et al. "Exceptionally potent neutralization of Middle East respiratory syndrome coronavirus by human monoclonal antibodies," Journal of Virology, vol. 88, issue 14 (Apr. 2014) pp. 7796-7805.
Tianlei Ying et al. "Monomeric IgG1 Fc molecules displaying unique Fc receptor interactions that are exploitable to treat inflammation-mediated diseases," mAbs, vol. 6, issue 5 (Sep./Oct. 2014) pp. 1201-1210.
Tianlei Ying et al. "Soluble Monomeric IgG1 Fc," The Journal of Biological Chemistry, vol. 287, No. 23 (Jun. 1, 2012) pp. 19399-19408.
Traxlmayr Michael W. et al., "Construction of a Stability Landscape of the CH3 Domain of Human IgG1 by Combining Directed Evolution with High Throughput Sequencing", Journal of Molecular Biology, (Oct. 2012), vol. 423, No. 3, , pp. 397-412.
Wang, X. et al., "lgG Fc Engineering to Modulate Antibody Effector Functions", Protein & Cell, (Oct. 6, 2017), vol. 1, No. 9, pp. 63-73, XP055457296.
Written Opinion of the International Searching Authority (Form PCT/ISA/237) for International Patent Application No. PCT/CN2022/094443, issued from the International Searching Authority, date of mailing Aug. 26, 2022, 11 pages.
Xu Wenxin, et al., "Efficacy and Mechanism-of-Action of a Novel Superagonist Interleukin-15: Interleukin-15 Receptor aSu/Fe Fusion complex in Syngeneic Murine Models of Multiple Myeloma," Cancer Research, vol. 73, No. 10, pp. 3077-3086, May 3, 2013.
Yu Deling, et al. "Advances in the Fc function and engineering modification of therapeutic monoclonal antibody", Chinese Journal of Histochemistry and Cytochemistry, (Dec. 31, 2019), vol. 28, No. 6, pp. 552-559.
European search report dated May 8, 2025 received in counterpart European Application No. 22810503.7 (3 pages).
European Search Report dated Dec. 11, 2024 received in European Application No. 21912542.4 (8 pages).
European Search Report for European Application No. 18870768.1; Application Filing Date Oct. 24, 2018; Date of Mailing May 26, 2021 (9 pages).
International Preliminary Report on Patentability (Form PCT/IB/373) for International Patent Application No. PCT/CN2022/086279, issued from the International Searching Authority, date of mailing Oct. 12, 2023, 11 pages.
International Search Report (Form PCT/ISA/210) for International Application No. PCT/CN2018/111577, issued from the International Searching Authority, date of mailing Jan. 29, 2019, with English-language translation, 8 pages.
International Search Report (Form PCT/ISA/210) for International Patent Application No. PCT/CN2021/076670, issued from the International Searching Authority, date of mailing Sep. 1, 2021 , with English-language translation, 14 pages.
International Search Report (Form PCT/ISA/210) for International Patent Application No. PCT/CN2021/076670, issued from the International Searching Authority, date of mailing Sep. 1, 2021, 9 pages.
International Search Report (Form PCT/ISA/210) for International Patent Application No. PCT/CN2022/086279, issued from the International Searching Authority, date of mailing May 7, 2022, with English-language translation, 7 pages.
International Search Report and Written Opinion issued in App. No. PCT/CN2018/111577, dated Jan. 29, 2019, 11 pages.
International Search Report and Written Opinion issued in App. No. PCT/CN2020/141250, date of mailing dated Jul. 30, 2021, 7 pages.
Office Action for Chinese Application No. 201711014953.3; Application Filing Date Oct. 26, 2017; Date of Mailing Mar. 25, 2020 (13 pages).
Office Action for Japanese Application No. 2020-541849; Application Filing Date Oct. 24, 2018; Date of Mailing May 11, 2021 (14 pages).
Written Opinion of the International Searching Authority (Form PCT/ISA/237) for International Patent Application No. PCT/CN2022/086279, issued from the International Searching Authority, date of mailing May 19, 2021, with English-language translation, 9 pages.
European Search Report dated May 6, 2025 received in EP Application No. 22787516 (10 pages).
Tang et al., "The challenges and molecular approaches surrounding interleukin-2-based therapeutics in cancer," Cytokine: X (2019) 1(1) 100001 (9 pages).

SEQUENCE LISTING

```
<160> NUMBER OF SEQ ID NOS: 17

<210> SEQ ID NO 1
<211> LENGTH: 114
<212> TYPE: PRT
<213> ORGANISM: Artificial Sequence
<220> FEATURE:
<223> OTHER INFORMATION: interleukin-15 mutant
<220> FEATURE:
<221> NAME/KEY: misc_feature
<222> LOCATION: (4)..(4)
<223> OTHER INFORMATION: Xaa can be Ala or Asn
<220> FEATURE:
<221> NAME/KEY: misc_feature
<222> LOCATION: (7)..(7)
<223> OTHER INFORMATION: Xaa can be Ser, Asp, or Tyr
<220> FEATURE:
<221> NAME/KEY: misc_feature
<222> LOCATION: (8)..(8)
<223> OTHER INFORMATION: Xaa can be Asp or Phe
<220> FEATURE:
<221> NAME/KEY: misc_feature
<222> LOCATION: (61)..(61)
<223> OTHER INFORMATION: Xaa can be Asp, Gly, or Asn
<220> FEATURE:
<221> NAME/KEY: misc_feature
<222> LOCATION: (64)..(64)
<223> OTHER INFORMATION: Xaa can be Glu or Tyr
<220> FEATURE:
<221> NAME/KEY: misc_feature
<222> LOCATION: (68)..(68)
<223> OTHER INFORMATION: Xaa can be Ile, Gln, or Lys
<220> FEATURE:
<221> NAME/KEY: misc_feature
<222> LOCATION: (72)..(72)
<223> OTHER INFORMATION: Xaa can be Asn or Tyr
<220> FEATURE:
<221> NAME/KEY: misc_feature
<222> LOCATION: (108)..(108)
<223> OTHER INFORMATION: Xaa can be Gln, Ser, Phe, or Ala
<220> FEATURE:
<221> NAME/KEY: misc_feature
<222> LOCATION: (109)..(109)
<223> OTHER INFORMATION: Xaa can be Met or His
<220> FEATURE:
<221> NAME/KEY: misc_feature
<222> LOCATION: (111)..(111)
<223> OTHER INFORMATION: Xaa can be Ile, Ala, or His

<400> SEQUENCE: 1

Asn Trp Val Xaa Val Ile Xaa Xaa Leu Lys Lys Ile Glu Asp Leu Ile
1               5                   10                  15

Gln Ser Met His Ile Asp Ala Thr Leu Tyr Thr Glu Ser Asp Val His
            20                  25                  30
```

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Xaa Thr Val Xaa
    50                  55                  60

Asn Leu Ile Xaa Leu Ala Asn Xaa Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Xaa Xaa Phe Xaa Asn
            100                 105                 110

Thr Ser


<210> SEQ ID NO 2
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 2

Asn Trp Val Ala Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 3
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 3

Asn Trp Val Asn Val Ile Asp Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
```

```
            100                 105                 110

Thr Ser


<210> SEQ ID NO 4
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 4

Asn Trp Val Asn Val Ile Tyr Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 5
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 5

Asn Trp Val Asn Val Ile Ser Phe Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 6
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 6
```

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Gly Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 7
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 7

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 8
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 8

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Tyr
    50                  55                  60
```

```
Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 9
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 9

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Gln Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 10
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 10

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Lys Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 11
```

```
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 11

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Tyr Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 12
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 12

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Ser Met Phe Ile Asn
            100                 105                 110

Thr Ser


<210> SEQ ID NO 13
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 13

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30
```

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Phe Met Phe Ile Asn
            100                 105                 110

Thr Ser


<210> SEQ ID NO 14
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 14

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Ala Met Phe Ile Asn
            100                 105                 110

Thr Ser


<210> SEQ ID NO 15
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 15

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95
```

-continued

```
Lys Glu Phe Leu Gln Ser Phe Val His Ile Val Gln His Phe Ile Asn
            100                 105                 110

Thr Ser


<210> SEQ ID NO 16
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 16

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ala Asn
            100                 105                 110

Thr Ser


<210> SEQ ID NO 17
<211> LENGTH: 114
<212> TYPE: PRT
<213> ORGANISM: Artificial Sequence
<220> FEATURE:
<223> OTHER INFORMATION: interleukin-15 mutant

<400> SEQUENCE: 17

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe His Asn
            100                 105                 110

Thr Ser
```

DEVELOPMENT AND USE OF INTERLEUKIN 15 MUTANT POLYPEPTIDE

CROSS REFERENCE TO RELATED APPLICATIONS

The present application is a section 371 of International Application No. PCT/CN2022/094443 filed May 23, 2022, which was published in the Chinse language on Dec. 1, 2022, under International Publication No. WO 2022/247778 A1, which claims the priority of Chinese patent application No. 202110591118.6 entitled "Development and Use of Novel Interleukin 15 Mutant Polypeptide," filed with the China Patent Office on May 28, 2021, the entire contents of which are incorporated herein by reference.

REFERENCE TO SEQUENCE LISTING SUBMITTED ELECTRONICALLY

This application contains a sequence listing, which is submitted electronically as an ASCII formatted sequence listing with a file name "069777-1US1 Substitute Sequence Listing" and a creation date of Oct. 3, 2024 and having a size of 19198 bytes. The sequence listing submitted via Patent Center is part of the specification and is herein incorporated by reference in its entirety.

TECHNICAL FIELD

The present invention belongs to the field of biotechnology, and specifically relates to a novel interleukin 15 mutant polypeptide, a preparation method thereof, and a nucleic acid, a plasmid, and a host cell required for constructing the novel interleukin 15 mutant polypeptide, as well as a corresponding pharmaceutical composition and uses thereof.

BACKGROUND ART

Interleukin 15 (IL-15) is a soluble cytokine found by Grabstein et al. in 1994 when detecting the supernatant of monkey kidney epidermal cell line CV21/EBNA. It can maintain the proliferation of CTLL-2 cells, and has attracted much attention as it has many similar biological activities with IL-2. Both IL-2 and IL-15 belong to the IL-2 family, and receptors for the IL-2 family members, including IL-2, IL-4, IL-7, IL-9, IL-15 and IL-21, all contain the γc chain. Among them, IL-2 and IL-15 share common IL-2/IL-15Rβ (CD122) and γc (CD132) receptors. The specific receptor for IL-2 is IL-2Rα (CD25), which is mainly expressed on the surface of activated T cells, and IL-2 is the most important cytokine to promote T cell proliferation. The specific receptor for IL-15 is IL15Rα (CD215).

In nature, IL-15 can bind to the IL-15β/γ receptor on the cell surface and activate the downstream STAT5 signaling pathway, which in turn promotes the differentiation and expansion of CD8+ T cells. IL-2 exists mainly in a free state in vivo, and therefore as long as it binds to the cell surface receptor, it can play its role. In contrast, IL-15 and IL-15Rα are mainly expressed on the surface of DC cells and monocytes, and exists rarely in a free state. Therefore, the activation of IL-15 signaling pathways is more likely to activate the downstream signaling pathways to function after cell-to-cell contact. IL-15 signaling is via the heterotrimeric complex of IL-15Rα, IL-15Rβ and γc. The mechanism of action of IL-15 is trans-presentation, that is, one cell presents its cell membrane-bound IL-15/IL-15Rα complex to another target cell expressing IL-15Rβ and γc receptors, which, in fact, is a "cell-to-cell" interaction. Trans-presentation requires that one cell must contact with another cell to function, which is not only required for regulating the body's immune system, but also to a certain extent, restricts the use of the IL-15/IL-15Rα complex for immunotherapy of related diseases.

Therefore, the development of a novel IL-15/IL-15Rα complex using synthetic biology techniques is of great significance. The present inventors have innovatively developed a novel monomeric Fc based on the antibody IgG's Fc in the field of long-acting proteins using synthetic biology (CN109705211B; 202011161007.3), which is introduced into the novel interleukin 15 mutant polypeptide of the present application. Moreover, by using the mechanism of action of trans-presentation of IL-15, the present inventors have innovatively developed a novel interleukin 15 mutant polypeptide with enhanced or reduced binding or biological activities for IL-15Rβ and γc receptors.

SUMMARY OF THE INVENTION

The main objectives of the present application are to provide a novel IL-15 mutant polypeptide and the use thereof.

In order to achieve the above objectives, the present invention provides the following technical solutions:

A novel IL-15 mutant polypeptide, comprising the amino acid sequence as set forth in SEQ ID NO: 1, wherein:

X1 is selected from any amino acid of A and N;
X2 is selected from any amino acid of S, D and Y;
X3 is selected from any amino acid of D and F;
X4 is selected from any amino acid of D, G and N;
X5 is selected from any amino acid of E and Y;
X6 is selected from any amino acid of I, Q and K;
X7 is selected from any amino acid of N and Y;
X8 is selected from any amino acid of Q, S, F and A;
X9 is selected from any amino acid of M and H; and
X10 is selected from any amino acid of I, A and H; and
the mutant polypeptide has increased or decreased binding activity for IL-15Rβ/γ compared to the naturally occurring IL-15 amino acid sequence.

As a preferred embodiment of the novel IL-15 mutant polypeptide as described above:

the novel IL-15 mutant polypeptide comprises the amino acid sequence as set forth in SEQ ID NO: 1, wherein X1 is A, X2 is S, X3 is D, X4 is D, X5 is E, X6 is I, X7 is N, X8 is Q, X9 is M, and X10 is I;

preferably, the novel IL-15 mutant polypeptide comprises the amino acid sequence as set forth in SEQ ID NO: 1, wherein X1 is N, X2 is selected from any amino acid of D and Y, X3 is D, X4 is D, X5 is E, X6 is I, X7 is N, X8 is Q, X9 is M, and X10 is I;

more preferably, the novel IL-15 mutant polypeptide comprises the amino acid sequence as set forth in SEQ ID NO: 1, wherein X1 is N, X2 is S, X3 is F, X4 is D, X5 is E, X6 is I, X7 is N, X8 is Q, X9 is M, and X10 is I;

further preferably, the novel IL-15 mutant polypeptide comprises the amino acid sequence as set forth in SEQ ID NO: 1, wherein X1 is N, X2 is S, X3 is D, X4 is selected from any amino acid of G and N, X5 is E, X6 is I, X7 is N, X8 is Q, X9 is M, and X10 is I; and still further preferably, the novel IL-15 mutant polypeptide comprises the amino acid sequence as set forth in SEQ ID NO: 1, wherein X1 is N, X2 is S, X3 is D, X4 is D, X5 is Y, X6 is I, X7 is N, X8 is Q, X9 is M, and X10 is I.

As a preferred embodiment of the novel IL-15 mutant polypeptide as described above: the novel IL-15 mutant polypeptide comprises the amino acid sequence as set forth in SEQ ID NO: 1, wherein X1 is N, X2 is S, X3 is D, X4 is D, X5 is E, X6 is selected from any amino acid of Q and K, X7 is N, X8 is Q, X9 is M, and X10 is I;

preferably, the novel IL-15 mutant polypeptide comprises the amino acid sequence as set forth in SEQ ID NO: 1, wherein X1 is N, X2 is S, X3 is D, X4 is D, X5 is E, X6 is I, X7 is Y, X8 is Q, X9 is M, and X10 is I;

more preferably, the novel IL-15 mutant polypeptide comprises the amino acid sequence as set forth in SEQ ID NO: 1, wherein X1 is N, X2 is S, X3 is D, X4 is D, X5 is E, X6 is I, X7 is Y, X8 is selected from any amino acid of S, F and A, X9 is M, and X10 is I;

further preferably, the novel IL-15 mutant polypeptide comprises the amino acid sequence as set forth in SEQ ID NO: 1, wherein X1 is N, X2 is S, X3 is D, X4 is D, X5 is E, X6 is I, X7 is N, X8 is Q, X9 is H, and X10 is I; and still further preferably, the novel IL-15 mutant polypeptide comprises the amino acid sequence as set forth in SEQ ID NO: 1, wherein X1 is N, X2 is S, X3 is D, X4 is D, X5 is E, X6 is I, X7 is N, X8 is Q, X9 is M, and X10 is selected from an amino acid of A and H.

```
(Amino acid sequence of IL-15 mutant)
                                         SEQ ID NO: 1
NWVX1VIX2X3LKKIEDLIQSMHIDATLYTESDVHPSCKVTAMKCFLLEL

QVISLESGDASIHX4TVX5NLIX6LANX7SLSSNGNVTESGCKECEELEE

KNIKEFLQSFVHIVX8X9FX10NTS

(Amino acid sequence of mutant B1-A1)
                                         SEQ ID NO: 2
NWVAVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

(Amino acid sequence of mutant B1-H4)
                                         SEQ ID NO: 3
NWVNVIDDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

(Amino acid sequence of mutant B1-H5)
                                         SEQ ID NO: 4
NWVNVIYDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

(Amino acid sequence of mutant B2-C1)
                                         SEQ ID NO: 5
NWVNVISFLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

(Amino acid sequence of mutant B2-G1)
                                         SEQ ID NO: 6
NWVNVISDLKKIEDLIQSMHIDATLYTESDVHPSCKVTAMKCFLLELQVI

SLESGDASIHGTVENLIILANNSLSSNGNVTESGCKECEELEEKNIKEFL

QSFVHIVQMFINTS
```

-continued

```
(Amino acid sequence of mutant B2-H1)
                                         SEQ ID NO: 7
NWVNVISDLKKIEDLIQSMHIDATLYTESDVHPSCKVTAMKCFLLELQVI

SLESGDASIHNTVENLIILANNSLSSNGNVTESGCKECEELEEKNIKEFL

QSFVHIVQMFINTS

(Amino acid sequence of mutant B3-A1)
                                         SEQ ID NO: 8
NWVNVISDLKKIEDLIQSMHIDATLYTESDVHPSCKVTAMKCFLLELQVI

SLESGDASIHDTVYNLIILANNSLSSNGNVTESGCKECEELEEKNIKEFL

QSFVHIVQMFINTS

(Amino acid sequence of mutant B4-B1)
                                         SEQ ID NO: 9
NWVNVISDLKKIEDLIQSMHIDATLYTESDVHPSCKVTAMKCFLLELQVI

SLESGDASIHDTVENLIQLANNSLSSNGNVTESGCKECEELEEKNIKEFL

QSFVHIVQMFINTS

(Amino acid sequence of mutant B4-B6)
                                        SEQ ID NO: 10
NWVNVISDLKKIEDLIQSMHIDATLYTESDVHPSCKVTAMKCFLLELQVI

SLESGDASIHDTVENLIKLANNSLSSNGNVTESGCKECEELEEKNIKEFL

QSFVHIVQMFINTS

(Amino acid sequence of mutant B4-E1)
                                        SEQ ID NO: 11
NWVNVISDLKKIEDLIQSMHIDATLYTESDVHPSCKVTAMKCFLLELQVI

SLESGDASIHDTVENLIILANYSLSSNGNVTESGCKECEELEEKNIKEFL

QSFVHIVQMFINTS

(Amino acid sequence of mutant R2-F7)
                                        SEQ ID NO: 12
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVSMFINTS

(Amino acid sequence of mutant R2-G7)
                                        SEQ ID NO: 13
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVFMFINTS

(Amino acid sequence of mutant R2-B9)
                                        SEQ ID NO: 14
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVAMFINTS

(Amino acid sequence of mutant R3-D1)
                                        SEQ ID NO: 15
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQHFINTS

(Amino acid sequence of mutant R4-E5)
                                        SEQ ID NO: 16
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFANTS
```

-continued (Amino acid sequence of mutant R4-G8)

SEQ ID NO: 17

NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFHNTS.

In a second aspect of the present invention, there is provided a nucleic acid molecule encoding the novel IL-15 mutant polypeptide as described above.

In a third aspect of the present invention, there is provided a plasmid, comprising the nucleic acid molecule as described above.

In a fourth aspect of the present invention, there is provided a host cell, comprising the plasmid as described above.

In a fifth aspect of the present invention, there is provided a fusion, formed by linking a fusion partner to the N-terminal and/or C-terminal of the novel IL-15 mutant polypeptide as described above; wherein

- the fusion partner is at least one of a heterologous protein, an adhesion molecule, a nucleic acid molecule, a small molecule compound, a toxin, an immune cell, and a detectable marker;
- the heterologous protein is an antibody, an antigen, a cytokine, a soluble receptor domain, a ligand, an enzyme, a peptide, or a protein domain, and the antigen is derived from an adenovirus-associated virus; and
- the immune cell is a chimeric antigen receptor T cell.

In a sixth aspect of the present invention, there is provided a pharmaceutical composition, comprising a prophylactically or therapeutically effective dose of the novel IL-15 mutant polypeptide as described above, or the fusion as described above, and a pharmaceutically acceptable carrier.

In a seventh aspect of the present invention, there is provided use of the IL-15 mutant polypeptide as described above or the pharmaceutical composition as described above in the preparation of a medicament for the treatment of a biological material.

In an eighth aspect of the present invention, there is provided a method for treating an autoimmune disease, an inflammatory disease, a neurodegenerative disease, a cancer or a pathogen infection, comprising administering to a subject a therapeutically effective amount of the novel IL-15 mutant polypeptide as described above, the nucleic acid molecule as described above, the plasmid as described above, or the fusion as described above.

In a ninth aspect of the present invention, there is provided a detection kit, comprising the novel IL-15 mutant polypeptide as described above, the nucleic acid molecule as described above, the plasmid as described above, or the fusion as described above; wherein

- the detection kit as described above is used for detecting a pathogen and a tumor cell.

Compared with the prior art, the present invention has the following beneficial effects: The present invention innovatively develops a novel interleukin 15 mutant polypeptide with enhanced binding or biological activities for IL-15Rγ and γc receptors, provides a nucleic acid sequence encoding the novel interleukin 15 mutant polypeptide and the amino acid sequence thereof, and in some embodiments, discloses a vector comprising the nucleic acid sequence and a host cell comprising the vector.

The present invention also discloses a pharmaceutical composition comprising the novel interleukin 15 mutant polypeptide. The antibody and composition disclosed herein can be used in the diagnosis and treatment of a disease. In embodiments, the novel interleukin 15 mutant polypeptide, the nucleic acid, the plasmid, and the vector are used for diagnosing or treating a related disease such as an autoimmune disease or a cancer.

DETAILED DESCRIPTION OF EMBODIMENTS

Figure 1A:
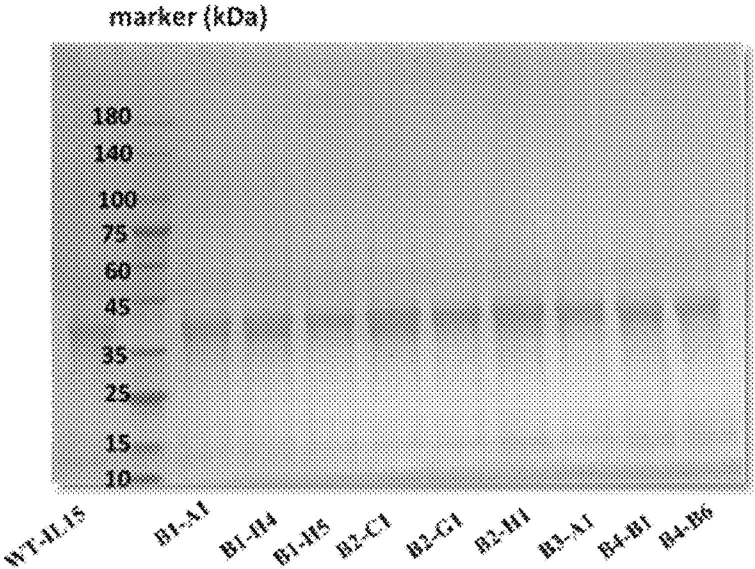
FIG. 1*a* shows the reduced SDS-PAGE analysis and Coomassie blue staining pattern of novel interleukin 15 mutant polypeptides (WT-IL15, B1-A1, B1-H4, B1-H5, B2-C1, B2-G1, B2-H1, B3-A1, B4-B1 and B4-B6).

In order to enable persons skilled in the art to better understand the solutions of the present application, the following clearly and completely describes the technical solutions in the embodiments of the present application with reference to embodiments. Apparently, the described embodiments are only a part of the embodiments of the present application, rather than all of the embodiments. Based on the embodiments of the present application, all other embodiments obtained by those of ordinary skill in the art without making creative efforts shall fall within the scope of protection of the present application.

In order that the present invention may be more thoroughly understood, some definitions are set forth below. Said definitions are intended to include grammatical equivalents.

As used herein, "N-terminal," also referred to as amino-terminus, $NH_2$-terminus, N-terminus or amine-terminus, is the start of a protein or polypeptide, and refers to the free amine group (—$NH_2$) at the terminus of a polypeptide. "C-terminal," also known as carboxy-terminus, carboxyl-terminus, C-terminal tail, C-terminus or COOH-terminus, is the terminus of a protein or polypeptide, terminated by a free carboxy (—COOH) terminus.

As used herein, "amino acid" means one of the 20 naturally occurring amino acids or any non-natural analog thereof, which may be located at a specified position.

By "protein" herein is meant at least two covalently linked amino acids, which includes proteins, polypeptides, oligopeptides and peptides. Proteins can be composed of naturally occurring amino acids and peptide bonds, or of synthetic peptide mimetic structures, i.e., "analogs".

As used herein, "nucleic acid" means a polymer composed of nucleotide units (ribonucleotides, deoxyribonucleotides, related naturally occurring structural variants, and synthetic non-naturally occurring analogs thereof) linked via phosphodiester bonds. Thus, the term includes polymers of nucleotides, in which the nucleotides and the linkages therebetween include non-naturally occurring synthetic analogs, such as, but not limited to, phosphorothioates, phosphoramidates, methylphosphonates, chiral methylphosphonates, 2'-O-methyl ribonucleotides, peptide nucleic acids (PNAs), and the like. For example, these polynucleotides can be synthesized using an automated DNA synthesizer. The term "oligonucleotide" generally refers to a short polynucleotide, typically no greater than about 50 nucleotides. It will be understood that when a nucleotide sequence is represented by a DNA sequence (i.e., A, T, G and C), this also includes RNA sequences in which "T" is replaced by "U" (i.e., A, U, G and C).

The regular notations are used herein to describe nucleotide sequences: the left-hand end of a single-stranded nucleotide sequence is referred to as the 5' end; and the left-hand direction of a double-stranded nucleotide sequence is referred to as the 5' direction. The direction in which nucleotides are added from 5' to 3' to the nascent RNA transcript is referred to as the direction of transcription. The DNA strand that has the same sequence as the mRNA is referred to as the coding strand.

As used herein, "encoding" means the intrinsic property of a particular nucleotide sequence in a polynucleotide, such as a gene, a cDNA or an mRNA, to be used as a template for the synthesis of other polymers and macromolecules in a biological process with a defined nucleotide sequence or a defined amino acid sequence, and biological properties resulting therefrom. Thus, a gene encodes a protein if transcription and translation of the mRNA produced by the gene produces the protein in a cell or other biological systems. The coding strand (whose nucleotide sequence is identical to the mRNA sequence and is usually provided in the sequence listing) and the non-coding strand (which is used as a transcription template of a gene or a cDNA) may be said to encode a protein, or other products of the gene or the cDNA. Unless otherwise specified, "a nucleotide sequence encoding an amino acid sequence" includes all nucleotide sequences that are degenerate versions of each other and that encode the same amino acid sequence. Nucleotide sequences that encode proteins and RNA may include introns.

As used herein, "plasmid" means a plasmid artificially constructed on the basis of a natural plasmid for adaptation to laboratory operations, through which a nucleic acid molecule can be introduced into a host cell, thereby producing a transformed host cell. A vector may include a nucleic acid sequence that allows it to replicate in a host cell, such as an origin of replication, and may also include one or more selectable marker genes and other genetic elements known in the art.

As used herein, "host cell", also referred to as recipient cell, refers to a host cell that receives a foreign gene in transformation and transduction (infection).

As used herein, "pharmaceutically acceptable carrier" means a regular pharmaceutically acceptable carrier. Remington's Pharmaceutical Sciences, E. W. Martin, Mack Publishing Co., Easton, Pa., 15th ed. (1975) describes compositions and formulations suitable for drug delivery of one or more therapeutic compounds or molecules, such as one or more antibodies, as well as additional agents.

As used herein, "preventing" a disease refers to inhibiting the full development of the disease. "Treatment" refers to a therapeutic intervention that ameliorates a sign or symptom of a disease or pathological condition after it has begun to develop.

By "prophylactically/therapeutically effective dose" herein is meant an amount of a particular agent sufficient to achieve the desired effects in a subject treated with the agent. The precise dosage will depend on the purpose of the treatment and can be determined by those skilled in the art using well known techniques. The dosage may be in the range of 0.01-100 mg/kg body weight or more, for example 0.1, 1, 10 or 50 mg/kg body weight, preferably 1-10 mg/kg. As is well known in the art, adjustments may be necessary for antibody or Fc fusion degradation, the rate of systemic or local drug delivery and new protease synthesis, as well as for age, body weight, general health, sex, diet, timing of administration, drug interactions, and severity of the condition, and can be determined by those skilled in the art using regular experimental methods.

By "autoimmune disease" herein is meant a disease in which the immune system generates an immune response (e.g., a B-cell or T-cell response) against a subset of antigens (i.e., self-antigens) of a normal host, with subsequent damage to the tissues. Self-antigens may be derived from host cells, or may be derived from commensal organisms, such as microorganisms that typically colonize mucosal surfaces (referred to as commensals). Autoimmune diseases affecting mammals include, but are not limited to, rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (e.g., Crohn's disease, and ulcerative colitis), autoimmune gastric atrophy, pemphigus vulgaris, psoriasis, vitiligo, type 1 diabetes, non-obese diabetes, myasthenia gravis, Graves disease, hashimoto's thyroiditis, sclerosing cholangitis, sclerosing salivary adenitis, systemic lupus erythematosus, autoimmune thrombocytopenic purpura, Goodpasture syndrome, Addison's disease, systemic sclerosis, polymyositis, dermatomyositis, autoimmune hemolytic anemia, pernicious anemia, and the like.

Preferably, the novel interleukin 15 mutant polypeptide of the present invention can be used to treat a cancer. The cancers as described in the present invention include, but are not limited to, lymphomas, blastomas, sarcomas (including liposarcomas), neuroendocrine tumors, mesotheliomas, schwannomas, meningiomas, adenomas, melanomas, and non-leukemic leukemias or lymphoid malignancies. More specific examples of the cancers as described above include squamous cell carcinomas (e.g., squamous epithelial cell carcinoma), lung cancer, small cell lung cancer, non-small cell lung cancer, lung adenocarcinoma and lung squamous cell carcinoma, peritoneal cancer, hepatocellular carcinoma, gastric cancer, gastrointestinal cancer, pancreatic cancer, malignant glioma, cervical cancer, ovarian cancer, liver cancer, bladder cancer, hepatoma, breast cancer, colon cancer, rectal cancer, colorectal cancer, endometrial or uterine cancer, salivary gland cancer, renal cancer, prostate cancer, vulva cancer, thyroid cancer, liver cancer, anal cancer, penis cancer, carcinoma of testis, esophageal cancer, bile duct tumor, head and neck cancer, bone marrow stromal tumor, osteoclastoma, multiple myeloma, osteolytic cancers (osteolytic bone cancers), central nervous system tumor, brain tumors (glioma, neuroblastoma, astrocytoma, medulloblastoma, ependymoma and retinoblastoma), nasopharyngeal carcinoma, basal cell carcinoma, cholangiocarcinoma, Kaposi's sarcoma, primary liver or endometrial carcinoma, and vascular tumors (angiosarcoma and hemagiopericytoma).

The present invention discloses a novel IL-15 mutant polypeptide, comprising the amino acid sequence as set forth in SEQ ID NO: 1, wherein:

X1 is selected from any amino acid of A and N;

X2 is selected from any amino acid of S, D and Y;

X3 is selected from any amino acid of D and F;

X4 is selected from any amino acid of D, G and N;
X5 is selected from any amino acid of E and Y;
X6 is selected from any amino acid of I, Q and K;
X7 is selected from any amino acid of N and Y;
X8 is selected from any amino acid of Q, S, F and A;
X9 is selected from any amino acid of M and H; and
X10 is selected from any amino acid of I, A and H; and
the mutant polypeptide has increased or decreased binding activity for IL-15Rβ/γ compared to the naturally occurring IL-15 amino acid sequence.

The present invention also discloses a nucleic acid molecule encoding the novel IL-15 mutant polypeptide as described above.

The present invention also discloses a plasmid, comprising the nucleic acid molecule as described above.

The present invention also discloses a host cell, comprising the plasmid as described above.

The present invention also discloses a fusion, formed by linking a fusion partner to the N-terminal and/or C-terminal of the novel IL-15 mutant polypeptide as described above; wherein the fusion partner is at least one of a heterologous protein, an adhesion molecule, a nucleic acid molecule, a small molecule compound, a toxin, an immune cell, and a detectable marker;

the heterologous protein is an antibody, an antigen, a cytokine, a soluble receptor domain, a ligand, an enzyme, a peptide, or a protein domain, and the antigen is derived from an adenovirus-associated virus; and the immune cell is a chimeric antigen receptor T cell.

The present invention also discloses a pharmaceutical composition, comprising a prophylactically or therapeutically effective dose of the novel IL-15 mutant polypeptide as described above, or the fusion as described above, and a pharmaceutically acceptable carrier.

The present invention also discloses use of the novel IL-15 mutant polypeptide as described above or the pharmaceutical composition as described above in the preparation of a medicament for the treatment of a biological material.

The present invention also discloses a method for treating an autoimmune disease, an inflammatory disease, a neurodegenerative disease, a cancer or a pathogen infection, comprising administering to a subject a therapeutically effective amount of the novel IL-15 mutant polypeptide as described above, the nucleic acid molecule as described above, the plasmid as described above, or the fusion as described above.

The present invention also discloses a detection kit, comprising the novel IL-15 mutant polypeptide as described above, the nucleic acid molecule as described above, the plasmid as described above, or the fusion as described above; wherein the detection kit as described above is used for detecting a pathogen and a tumor cell.

Standard recombinant DNA techniques and molecular cloning techniques used in the Examples are well known in the art (Ausubel, F. M. et al., Current Protocols in Molecular Biology, published by Greene Publishing Assoc. and Wiley-Interscience), and materials and methods suitable for microbial growth are well known in the art. The main chemical and biological reagents were purchased from KAPA Biosystems, New England Biolabs, TransGen Biotech, Thermo Fisher Scientific, OMEGA bio-tek, etc.

The present invention will be described in detail below with reference to specific examples.

Example 1: Design and Construction of Novel Interleukin 15 Mutant Library

According to the crystalline complex structure (PDB ID: 4GS7) of IL-15 and its receptors α, β and γ, the three receptors bind to three different positions of IL-15, respectively. Therefore, when the interface residues of IL-15 and its receptors β and γ are modified, the binding of IL-15 to receptor a will not be affected.

Therefore, we used the crystal structure to determine the key sites for the interaction of IL-15 with its receptor β to be N4, S7, D8, D61, E64, N65, 168 and N72, and the key sites for the interaction of IL-15 with its receptor γ to be D30, H32, Q108, M109, I111 and N112.

After selecting the key sites of action, we designed and used degenerate amino acid primers to introduce random site-directed mutations at the key amino acid sites, and constructed them into the phage expression vector pComb3x. We innovatively used monoclonal protein capture ELISA, in which IL-15Rβ and γc receptors were used as capture antigens, with which the selected monoclones mutated at key sites were reacted to preliminarily determine the affinity of these novel IL-15 mutants for receptor β and γ, and the wild-type IL-15 was used as control.

Figure 1B:
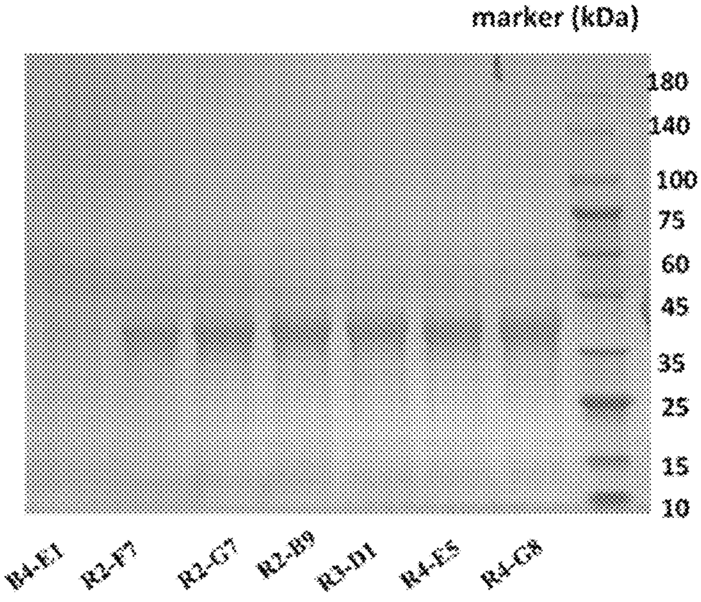
FIG. 1*b* shows the reduced SDS-PAGE analysis and Coomassie blue staining pattern of novel interleukin 15 mutant polypeptides (B4-E1, R2-F7, R2-G7, R2-B9, R3-D1, R4-E5 and R4-G8).

The positive cloned genes were cloned into the eukaryotic expression vector PTT, the successfully constructed plasmids were extracted and transiently co-transformed into Expi293 cells for expression, and purified by protein G resin (YING Tianlei et al., JOURNAL OF BIOLOGICAL CHEMISTRY, 2012, 287(23): 19399-19408). The purity of the purified proteins was verified by SDS-PAGE gel, and the results were shown in FIG. 1.

Example 2: Detection of Binding Ability of Novel IL-15 Mutant Polypeptides to IL-15Rβ by Bio-Layer Interferometry (BLI)

The Anti-human IgG Fc Capture (AHC) probe (purchased from GE) was used to detect the respective binding ability of the novel interleukin 15 mutant polypeptides to IL-15Rβ.

The expression and preparation of the novel interleukin 15 mutant polypeptides in a soluble form were substantially carried out according to the literature (YING Tianlei et al., JOURNAL OF BIOLOGICAL CHEMISTRY, 2012, 287 (23): 19399-19408). During the detection procedure, the novel interleukin 15 mutant polypeptides were diluted at a ratio of 1:3 (the initial concentration for the detection of the affinity for IL-15Rβ was 1000 nM, which was serially diluted to 12.35 nM).

Figure 2A:
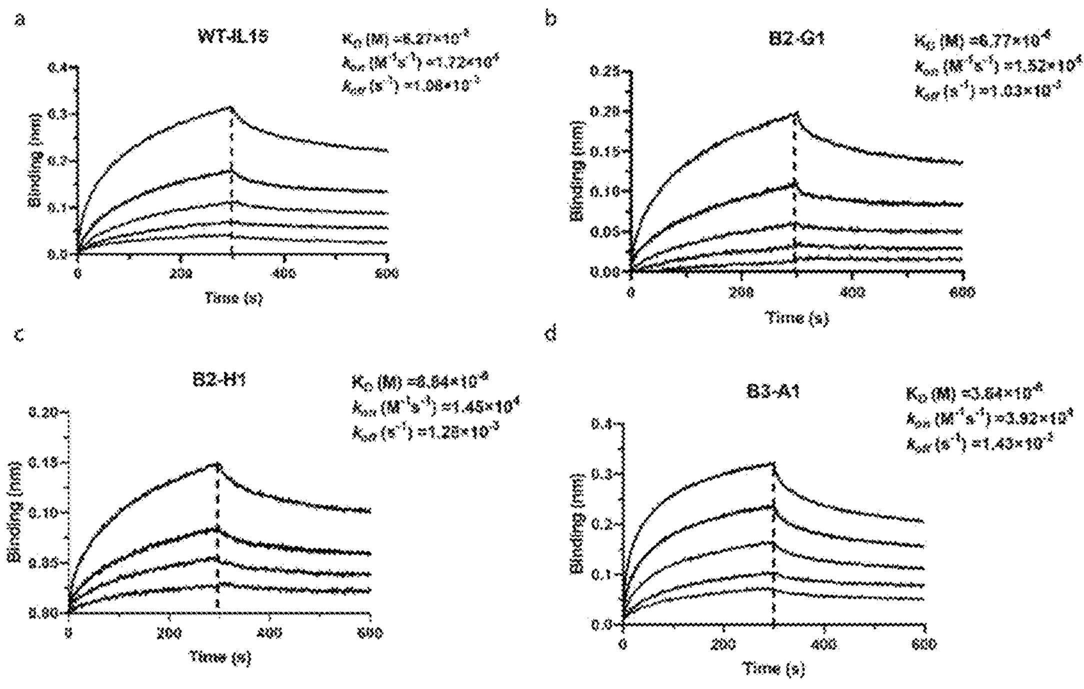
FIG. 2*a* shows the affinity of novel interleukin 15 mutant polypeptides (WT-IL15, B2-G1, B2-H1 and B3-A1) for IL-15Rβ as detected by Bio-Layer Interferometry (BLI).
Figure 2B:
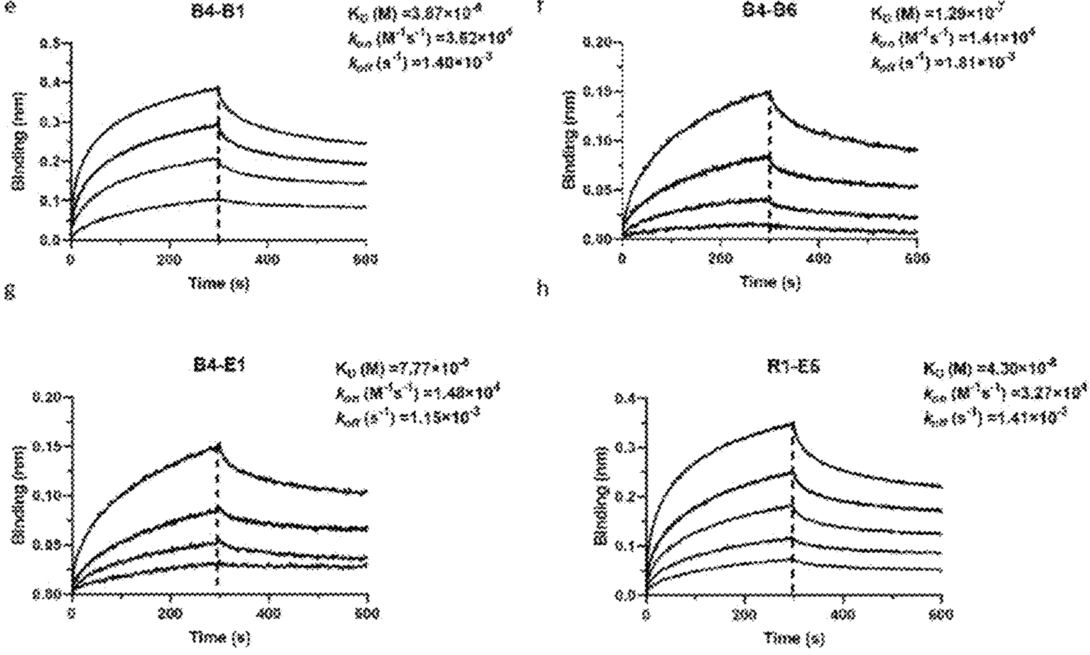
FIG. 2*b* shows the affinity of novel interleukin 15 mutant polypeptides (B4-B1, B4-B6, B4-E1 and R1-E5) for IL-15Rβ as detected by Bio-Layer Interferometry (BLI).

As shown in the results of FIG. 2, the novel interleukin 15 mutant polypeptides had increased or decreased binding to IL-15Rβ due to mutations at the key amino acid sites for binding to IL-15Rβ.

Example 3: Evaluation of Biological Activity of Novel IL-15 Mutant Polypeptides in Cell Line CTLL-2

To evaluate the biological activity of the novel IL-15 mutant polypeptides, a proliferation assay on cell line CTLL-2 was used. Biological activity was measured by the stimulation of the proliferation of these cells using mitochondrial staining with 3-(4,5-dimethylthiazol-2-yl)-2,5-diphenyltetrazolium bromide (MTT) (Mossman T. J. Immunol. Methods. 1983, 65(1-2): 55-63) according to the procedure described below.

Serial dilutions (starting from a concentration of 4 μg/mL) were performed on B1-A1, B1-H4, B1-H5, B2-C1, B2-G1, B2-H1, B3-A1, B4-B1, B4-B6, B4-E1, R2-F7, R2-G7, R2-B9, R3-D1, R4-E5, R4-G8, WT-15 and sFc in 50 μL of RPMI medium supplemented with 10% fetal bovine serum (FBS) and 50 μg/mL gentamicin in a 96-well culture plate (Costar, USA). CTLL-2 cells were pre-washed 5 times with RPMI medium and added to the plate at $5\times10^3$ cells/well in a volume of 50 μL.

Figure 3:
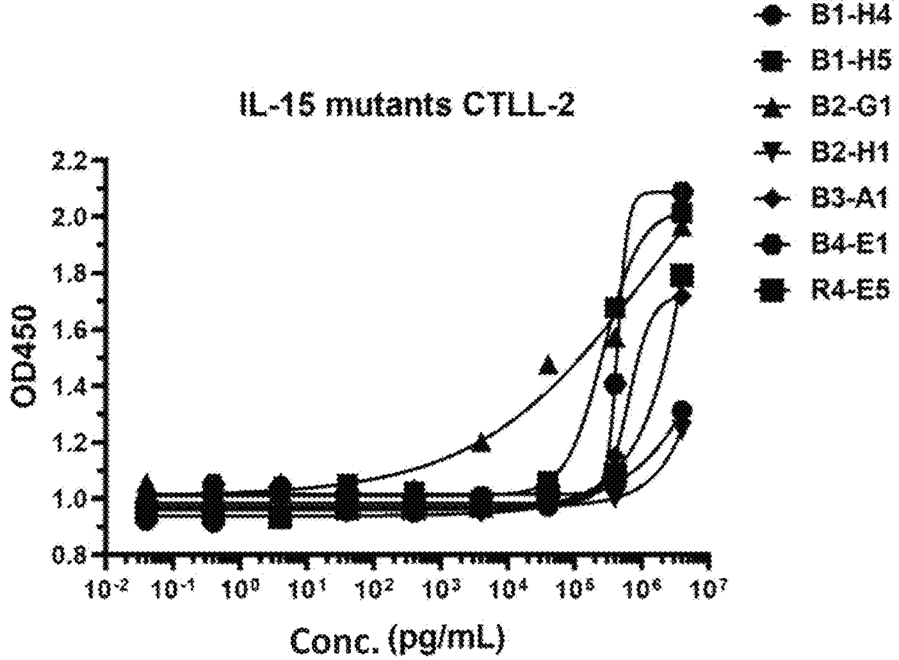
FIG. 3 shows the biological activity of novel interleukin 15 mutant polypeptides as evaluated by a proliferation assay on CTLL-2.

The plate was incubated for 72 hours at 5% $CO_2$ and 98% relative humidity at 37° C. Cell viability was determined by staining with MTT. sFc was not biologically active, because it did not induce the proliferation of CTLL-2 cells, unlike B1-H4, B1-H5, B2-G1, B2-H1, B3-A1, B4-E1 and R4-E5, which stimulated proliferation in a dose-dependent manner, as shown in the results of FIG. 3.

The above description of the disclosed embodiments enables those skilled in the art to implement or use the present invention. The above description is only a preferred implementation of the present invention, and it should be pointed out that for those skilled in the art, several improvements and supplements can be also made without departing from the principles of the present invention, which should also be regarded to fall within the scope of protection of the present invention. Various modifications to these embodiments will be readily apparent to those skilled in the art, and the generic principles defined herein may be implemented in other embodiments without departing from the spirit or scope of the present invention. Thus, the present invention will not be limited to the embodiments shown herein, but is to conform to the widest range consistent with the principles and novel features disclosed herein.

The invention claimed is:

1. An interleukin-15 (IL-15) mutant polypeptide, comprising an amino acid sequence selected from SEQ ID NOs: 2-17.

2. The IL-15 mutant polypeptide of claim 1, comprising the amino acid sequence of SEQ ID NO: 3.

3. The IL-15 mutant polypeptide of claim 1, comprising the amino acid sequence of SEQ ID NO: 4.

4. The IL-15 mutant polypeptide of claim 1, comprising the amino acid sequence of SEQ ID NO: 6.

5. The IL-15 mutant polypeptide of claim 1, comprising the amino acid sequence of SEQ ID NO: 7.

6. The IL-15 mutant polypeptide of claim 1, comprising the amino acid sequence of SEQ ID NO: 8.

7. The IL-15 mutant polypeptide of claim 1, comprising the amino acid sequence of SEQ ID NO: 9.

8. The IL-15 mutant polypeptide of claim 1, comprising the amino acid sequence of SEQ ID NO: 10.

9. The IL-15 mutant polypeptide of claim 1, comprising the amino acid sequence of SEQ ID NO: 11.

10. The IL-15 mutant polypeptide of claim 1, comprising the amino acid sequence of SEQ ID NO: 16.

11. An isolated nucleic acid molecule, encoding the IL-15 mutant polypeptide according to claim 1.

12. An isolated plasmid, comprising the nucleic acid molecule according to claim 11.

13. An isolated host cell, comprising the nucleic acid molecule according to claim 11.

14. An isolated host cell, comprising the plasmid according to claim 12.

15. A fusion, formed by linking a fusion partner to the N-terminal and/or C-terminal of the IL-15 mutant polypeptide according to claim 1, wherein the fusion partner is a heterologous molecule.

16. A pharmaceutical composition, comprising the IL-15 mutant polypeptide according to claim 1, and a pharmaceutically acceptable carrier.

17. A pharmaceutical composition, comprising the fusion according to claim 15, and a pharmaceutically acceptable carrier.

18. A kit, comprising the IL-15 mutant polypeptide according to claim 1.

19. A kit, comprising the fusion according to claim 15.

* * * * *